(12) United States Patent
Goutsis et al.

(10) Patent No.: US 10,105,308 B2
(45) Date of Patent: Oct. 23, 2018

(54) TEMPORARY CHANGING THE COLOR OF HAIR USING PIGMENTS, ALCOHOLS AND ZWITTERIONIC POLYMERS

(71) Applicant: Henkel AG & Co. KGaA, Duesseldorf (DE)

(72) Inventors: Konstantin Goutsis, Juechen (DE); Gabriele Weser, Neuss (DE)

(73) Assignee: Henkel AG & Co. KGaA (DE)

(*) Notice: Subject to any disclaimer, the term of this patent is extended or adjusted under 35 U.S.C. 154(b) by 0 days.

(21) Appl. No.: 15/492,880

(22) Filed: Apr. 20, 2017

(65) Prior Publication Data

US 2017/0216184 A1 Aug. 3, 2017

Related U.S. Application Data

(63) Continuation of application No. PCT/EP2015/071725, filed on Sep. 22, 2015.

(30) Foreign Application Priority Data

Oct. 23, 2014 (DE) .................. 10 2014 221 535

(51) Int. Cl.
| | |
|---|---|
| A61Q 5/10 | (2006.01) |
| A61K 8/81 | (2006.01) |
| A61Q 5/06 | (2006.01) |
| A61K 8/34 | (2006.01) |
| A61K 8/29 | (2006.01) |
| A61K 8/25 | (2006.01) |
| A61K 8/19 | (2006.01) |
| A61K 8/26 | (2006.01) |

(52) U.S. Cl.
CPC ............. *A61K 8/8158* (2013.01); *A61K 8/19* (2013.01); *A61K 8/25* (2013.01); *A61K 8/26* (2013.01); *A61K 8/29* (2013.01); *A61K 8/345* (2013.01); *A61Q 5/06* (2013.01); *A61Q 5/065* (2013.01); *A61K 2800/43* (2013.01); *A61K 2800/805* (2013.01)

(58) Field of Classification Search
CPC ........ A61K 8/8158; A61K 8/345; A61K 8/29; A61K 8/25; A61K 8/26; A61K 2800/43; A61K 2800/805; A61Q 5/065
See application file for complete search history.

(56) References Cited

U.S. PATENT DOCUMENTS

| | | | |
|---|---|---|---|
| 6,042,619 A | 3/2000 | Haning et al. | |
| 6,190,648 B1* | 2/2001 | Kouzu | A61K 8/898 424/70.11 |
| 2013/0000662 A1* | 1/2013 | Goutsis | A61Q 5/10 132/208 |

FOREIGN PATENT DOCUMENTS

| | | |
|---|---|---|
| EP | 0887067 A2 | 12/1998 |
| FR | 2709418 A1 | 3/1995 |

OTHER PUBLICATIONS

STIC Search Report dated Jul. 11, 2017.*
PCT International Search Report (PCT/EP2015/071728) dated Nov. 18, 2015.
Database CA [Online] Chemical Abstracts Service, Columbus, Ohio, US; 2006, "Temporary hair dye preparations containing ethanol, black titanium oxide, polymers, and glycerin", XP002749399, Database accession No. 148:386501 abstract & JP 2008 063251 A (Tokiwa Corp; Kao Corp) Mar. 21, 2008 (Mar. 21, 2008).
Database WPI Week 200570 Thomson Scientific, London, GB; AN 2005-678469, XP002749400, "Gel-like hair-dye composition, contains pigment and/or carbon black having pearl glossiness, gelatinizer, film forming polymer, and silicone modified polymer obtained by reacting amino- and anion-group containing polymers", & JP 2005 239626 A Sep. 8, 2005 (Sep. 8, 2005) abstract.
Database CA [Online] Chemical Abstracts Service, Columbus, Ohio, US; 1999, "Hair dyes containing amphoteric polymers", XP002749401, Database accession No. 131:9443 abstract & JP HII 124319 A (Shiseido Co Ltd) May 11, 1999 (May 11, 1999).
Database CA [Online] Chemical Abstracts Service, Columbus, Ohio, US; 2008, "Manufacture of temporary hair dye preparations containing pigments", XP002749402, Database accession No. 148:338286 abstract & JP 2008 063252 A (Kao Corp; Tokiwa Corp) Mar. 21, 2008 (Mar. 21, 2008).
Anonymous: "Methacryloyl Ethyl Betaine/Acrylates Copolymer", Personal Care Products Council, XP002749403, Retrieved from the Internet: URL:http://webdictionary.personalcarecouncil.org/jsp/IngredientDetail.jsp?monoid=3632 [retrieved on Oct. 29, 2015] the whole document.
"International Cosmetic Ingredient Dictionary and Handbook", 2012, Personal Care Products Council, XP002749404, vol. 1. p. 56, Eintrag "Acrylamidopropyltrimonium Chloride/Acrylates Copolymer", Abschnitt "Reported Functions".
Database CA [Online] Chemical Abstracts Service. Columbus, Ohio. US; "Temporary dyeing compositions for the hair", XP002749405, Database accession No. 115:119836 abstract & JP H03 141216 A (Mitsubishi Petrochemical Co) Jun. 17, 1991 (Jun. 17, 1991).

* cited by examiner

Primary Examiner — Eisa B Elhilo
(74) Attorney, Agent, or Firm — James J. Cummings

(57) ABSTRACT

An agent for temporarily changing the color of keratin fibers, in particular human hair, include in an aqueous cosmetic carrier (a) at least one aliphatic and/or aromatic alcohol having 2-8 C atoms (b), at least one color pigment, and (c) at least one zwitterionic polymer, the total weight of the solid matter (d) included in the agent, with respect to the total weight of the agent, being less than 2.5 wt. %.

15 Claims, No Drawings

TEMPORARY CHANGING THE COLOR OF HAIR USING PIGMENTS, ALCOHOLS AND ZWITTERIONIC POLYMERS

FIELD OF THE INVENTION

The present invention generally relates to agents for temporarily changing the color of keratinic fibers, in particular human. A further subject of this invention is a method for changing the color of and for styling hair, a suitable agent being sprayed onto the hair and the hair being simultaneously arranged into a hairstyle.

BACKGROUND OF THE INVENTION

The changing of the shape and color of keratinic fibers, particularly of hair, is an important field in modern cosmetics. To change the hair color, the skilled artisan is familiar with a variety of dyeing systems depending on the dyeing requirements. Oxidation dyeing agents are typically used for permanent, intense colors with good fastness properties and good gray coverage. Such dyeing agents typically include oxidation dye precursors, so-called developer components and coupler components, which together form the actual dyes under the influence of oxidizing agents, such as, for example, hydrogen peroxide. Oxidation dyeing agents are characterized by very long-lasting coloring results.

When direct dyes are used, already formed dyes diffuse out of the dyeing agent into the hair fiber. In comparison with oxidative hair coloring, the colors obtained with direct dyes have a lower durability and a more rapid washing out. Colors with direct dyes typically remain on the hair for a time period between 5 and 20 shampooings.

In the context of modern fashion trends, there is also the desire for color effects, which remain on the hair for a short time period and can be removed again thereafter from the hair without any residues by shampooing. Direct dyes diffuse more or less greatly into the hair fiber and outlast many shampooings there; this dye class is therefore not highly suitable for the residue-free removal of the color effect.

Using color pigments for a brief color change to hair is known. Color pigments are generally understood to be insoluble, color-imparting substances. They are present undissolved in the form of small particles in the dye formulation; these particles only attach to the hair fibers from the outside. They remain there until the next hair washing and can be removed again without residues by shampooing. Various products of this type can be obtained on the market under the name hair mascara.

Because the removal of hair mascara is possible by washing the hair, they are usually conceptualized as "leave-on" products. It is of particular advantage for the user of a "leave-on" product, if he/she can also undertake an easy temporary styling of the hair simultaneously with the temporary change in color. Styling such as curling, straightening, teasing, or setting as well are considerations, for example, as temporary hairstyles. Temporary hairstyles can be achieved, for example, by styling agents, such as hairsprays, hair waxes, hair gels, setting lotions, blow-dry waves, styling sprays, etc. Temporary styling is also called hair styling or styling and the hairstyling agents are also called styling products.

Products that permit simultaneous changing of the color and shape are already known from the prior art. For example, hair mascara products, which include pigments together with nonionic polymers and high-melting waxes, are described in WO 9920230 A2.

WO 2014146818 A1 also discloses styling agents with pigments, which are characterized by the presence of solid fatty alcohols and waxes.

The fat and wax components included in these products usually serve to adjust a specific drying time, by which the consumer in fact experiences the feeling of dry hair, but the mascara applied to the hair retains residual moisture due to which the hairstyle remains shapeable and combable.

Even in the case of products remaining on the hair, however, there is often the problem as well that the hair is weighed down by the presence of the fatty substances. The impression of "oily hair" arises visually, and the setting properties of these products are relatively poor. There is, furthermore, still a potential for improvement in the case of combination products for color changing and for styling.

Accordingly, it is desirable to provide a hair mascara product with a versatile use, which enables the temporary changing of hair color. The hair mascara should be packageable so that it can be applied by a sponge, brush, and also as a spray application. The color change in this case should occur easily and with little damage and be again removable from the hair without any residues by washing. The product on the hair should be extremely resistant to external influences until the time of the next shampooing, however; i.e., color loss or other detachment of the product should not become visible either by rubbing off on textiles or by combing. At the same time, the hair dyed in this way should have a soft feel, not be weighed down, not feel hard or oily, and also not give the impression visually of oily hair. Furthermore, other desirable features and characteristics of the present invention will become apparent from the subsequent detailed description of the invention and the appended claims, taken in conjunction with this background of the invention.

BRIEF SUMMARY OF THE INVENTION

A first subject of the present invention is an agent for temporarily changing the color of keratinic fibers, in particular human hair, including, in an aqueous cosmetic carrier,
 (a) at least one aliphatic and/or aromatic alcohol having 2 to 8 C atoms,
 (b) at least one color pigment, and
 (c) at least one zwitterionic polymer,
wherein the total amount of fatty substances (d), included in the agent, based on the total weight of the agent, has a value below 2.5% by weight.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It emerged surprisingly that these objects can be achieved by using color pigments and specific zwitterionic polymers, if these are used in a special aqueous-alcoholic carrier characterized by a low content of fatty substances.

Keratinic fibers, keratin-containing fibers, or keratin fibers are to be understood to mean pelts, wool, feathers, and in particular human hair. Although the agents of the invention are primarily suitable for lightening and dyeing keratin fibers, in principle nothing precludes a use in other fields as well.

The term "temporary color change" in the context of this invention is understood to mean a temporary coloring of the hair, which can be removed completely or nearly completely by shampooing (with a commercial shampoo). The term "temporary color change" in the context of the present invention does not include oxidative dyeing carried out with oxidation dyes. Likewise, the term "temporary color change" does not include lightening, bleaching, or blonding of keratin fibers caused by the use of an oxidizing agent. Both the effect caused by the oxidative color change and the one caused by blonding cannot be reversed by the washing of hair, and both color changes are therefore not temporary.

The agents include the ingredients essential to the invention in each case in an aqueous cosmetic carrier. For the purpose of the temporary change in color and shape, carriers of this type can be, for example, gels or also surfactant-containing foaming solutions, such as, for example, shampoos, sprayable solutions, foam aerosols, or foam formulations.

The agents of the invention include at least one aliphatic and/or aromatic alcohol having 2 to 8 C atoms as the first ingredient (a) essential to the invention. Aliphatic and/or aromatic alcohols having 2 to 8 C atoms are compounds that have 2 to 8 C atoms, are aliphatic and/or aromatic in nature, and carry one or more hydroxy groups.

The alcohols (a) in the context of the present invention carry no heteroatoms different from oxygen. They can include an ether grouping, but moreover have no functional groups that are different from the hydroxy group (i.e., monoethanolamine, alpha-hydroxycarboxylic acids, dihydroxyacetone, etc., are not alcohols in the context of the present invention).

Suitable aliphatic alcohols are, for example, ethanol, isopropanol, n-propanol, butanol, n-pentanol, 1,2-propanediol, 1,3-propanediol, 1,3-butanediol, 1,4-butanediol, 1,2-hexanediol, 1,6-hexanediol, and glycerol. Suitable aromatic alcohols are, for example, benzyl alcohol, phenoxyethanol, and phenethyl alcohol.

In one embodiment, an agent of the invention for temporarily changing the color of keratinic fibers is characterized in that it includes one or more alcohols (a) from the group comprising ethanol, isopropanol, n-propanol, butanol, n-pentanol, 1,2-propanediol, 1,3-propanediol, 1,3-butanediol, 1,4-butanediol, 1,2-hexanediol, 1,6-hexanediol, glycerol, benzyl alcohol, phenoxyethanol, and phenethyl alcohol.

The alcohols (a) of the invention are organic solvents, which contribute to the solution of the zwitterionic polymers (c) and after application of the agent to the keratinic fiber influence the speed of film formation by zwitterionic polymers (c). It emerged that this film formation proceeds especially well and is especially uniform, if the agent includes the alcohol(s) in a minimum amount of at least 10.0% by weight. The best results were observed with an alcohol amount of at least 40% by weight. All quantitative data given in % by weight in this case are based on the total amount of all alcohols (a) of the invention, which is placed in relation to the total weight of the agent.

In a preferred embodiment, an agent of the invention is characterized in that, based on its total weight, it includes one or more alcohols (a) in a total amount of at least 10.0% by weight, preferably of at least 20.0% by weight, more preferably of at least 30.0% by weight, even more preferably of at least 40.0% by weight, and very particularly preferably of at least 50.0% by weight.

The alcohols from group (a) are compounds that have different boiling points and different degrees of volatility. It emerged that within this group ethanol is the most suitable. If the agents include significant amounts of ethanol, the pigments deposited on the keratin fibers are surrounded by a polymer film of zwitterionic polymers (c), which are formed such that the pigments adhere especially well to the keratin fibers. In this case, the coloring result is especially uniform and the rubbing off of the pigments caused by rubbing on textiles is minimized.

In a very particularly preferred embodiment, an agent of the invention is therefore characterized in that, based on its total weight, it includes at least 15.0% by weight, preferably at least 25.0% by weight, more preferably at least 35.0% by weight, and very particularly preferably at least 45.0% by weight of ethanol.

The previously described properties can be improved still further, if a further polyhydric alcohol with a low volatility, for example, 1,2-propanediol or glycerol, is added to the ethanol in a smaller amount.

In a further very particularly preferred embodiment, an agent of the invention is therefore characterized in that, based on its total weight, it includes 1,2-propanediol and/or glycerol in a total amount of 0.1 to 7.0% by weight, preferably 0.5 to 5.5% by weight, more preferably 1.0 to 3.5% by weight, and particularly preferably 1.5% by weight to 2.5% by weight. The agents of the invention include all essential ingredients in an aqueous carrier. The water content of the agent can also influence the deposition of the pigments on the keratin fibers and the film formation of the zwitterionic polymers (c). If the water content is too high, there is the risk that the product does not dry sufficiently rapidly. In particular, if the agents were adjusted to a low viscosity (for example, because they are to be sprayed), the coloring result can then be more nonuniform. A water content between 20 and 60% by weight, preferably between 24 and 54% by weight, more preferably between 28 and 50% by weight, and particularly preferably between 32 and 42% by weight has emerged as highly suitable in this regard. The water content given in % by weight in this case refers to the amount of water included the total weight of the agent.

In a further very particularly preferred embodiment, an agent of the invention for a temporary color change is therefore characterized in that, based on its total weight, it has a water content between 20 and 60% by weight, preferably between 24 and 54% by weight, more preferably between 28 and 50% by weight, and particularly preferably between 32 and 42% by weight.

The agents for the temporary color change include at least one color pigment (b) as the second component essential to the invention. A pigment in the context of the present invention is understood to be a color-imparting compound that has a solubility in water of less than 0.1 g/L at 20° C.

The following method can be used for determining the water solubility of the pigment: 0.1 g of the pigment is weighed in a beaker. A stir bar is added. Then, the mixture is topped up with distilled water (20° C.) to 1 L. The mixture is stirred for an hour. If after this time period still undissolved parts of the pigment are visible in the mixture, thus the solubility of the pigment is below 0.1 g/L.

A temporary coloring is to occur with the agents of the invention. The creation of "metallic" effects in particular is in the foreground in this regard. White pigments are therefore not included in the definition of color pigments. White pigments are achromatic inorganic pigments with a high refractive index (generally greater than 1.8), which are usually produced synthetically and are used primarily for creating optical whiteness in coating compositions or as fillers in, e.g., plastics. White pigments, such as, for example, titanium dioxide or zinc dioxide are not explicitly covered by the definition of a color pigment.

The color pigments are present in the agents in the form of small undissolved particles, which do not diffuse into the hair fiber, but under effect of the zwitterionic polymer(s) (c) are deposited on the outer wall of the keratin fibers and are held there by the polymer film. Suitable color pigments can be organic and/or inorganic in origin.

Because of their excellent light, weather, and/or temperature resistance, the use of inorganic color pigments is particularly preferred in the method of the invention. The preferred average particle size of the (preferably inorganic) color pigments is 0.1 μm to 1 mm, more preferably of 0.5 μm to 750 μm, and in particular 10 μm to 500 μm.

Preferred color pigments are selected from inorganic pigments that may be synthetic or natural in origin. Inorganic color pigments of natural origin can be produced, for example, from chalk, ocher, umber, green earth, burnt sienna, or graphite. Furthermore, black pigments, such as, e.g., iron oxide black, many-colored pigments, such as, e.g., ultramarine or iron oxide red, as well as fluorescent or phosphorescent pigments, can be used as inorganic color pigments.

Especially suitable are colored metal oxides, hydroxides, and oxide hydrates, mixed phase pigments, sulfur-containing silicates, silicates, metal sulfides, complex metal cyanides, metal sulfates, chromates, and/or molybdates. Particularly preferred color pigments are black iron oxide (CI 77499), yellow iron oxide (CI 77492), red and brown iron oxide (CI 77491), manganese violet (CI 77742), ultramarine (sodium aluminum sulfosilicate, CI 77007, Pigment Blue 29), chromium oxide hydrate (CI77289), iron blue (Ferric Ferrocyanide, CI77510), and/or carmine (cochineal).

Color pigments particularly preferred according to the invention are colored pearlescent pigments. These are typically based on mica and can be coated with one or more metal oxides from the group comprising titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicate, CI 77007, Pigment Blue 29), chromium oxide hydrate (CI 77289), chromium oxide (CI 77288), and/or iron blue (Ferric Ferrocyanide, CI 77510).

Mica is a phyllosilicate. The most important representatives of these silicates are muscovite, phlogopite, paragonite, biotite, lepidolite, and margarite. To produce the pearlescent pigments in conjunction with metal oxides, mica, primarily muscovite or phlogopite, is coated with a metal oxide.

Alternatively to natural mica, synthetic mica optionally coated with one or more metal oxide(s) can also be used as a pearlescent pigment. Such suitable pearlescent pigments based on natural mica are described in the Unexamined German Patent Application WO 2005065632, to which reference is expressly made. Particularly preferred pearlescent pigments are based on natural or synthetic mica and are coated with one or more of the aforementioned metal oxides. The color of the particular pigments can be varied by varying the layer thickness of the metal oxide(s).

In a further particularly preferred embodiment, an agent of the invention is characterized in that it includes as color pigment (b) at least one inorganic color pigment, which is selected from colored metal oxides, metal hydroxides, metal oxide hydrates, silicates, metal sulfides, complex metal cyanides, metal sulfates, bronze pigments, and/or colored mica-based pigments, which are coated with at least one metal oxide and/or a metal oxychloride.

In a further very particularly preferred embodiment, an agent of the invention is characterized in that it includes as color pigment (b) at least one mica-based color pigment, which is coated with one or more metal oxides from the group comprising titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicate, CI 77007, Pigment Blue 29), chromium oxide hydrate (CI 77289), chromium oxide (CI 77288), and/or iron blue (Ferric Ferrocyanide, CI 77510). Examples of particularly suitable color pigments are obtainable commercially, for example, under the trade names: Rona®, Colorona®, Dichrona®, and Timiron® from the company Merck, Ariabel® and Unipure® from the company Sensient, Prestige® from the company Eckart Cosmetic Colors, and Sunshine® from the company Sunstar.

Very particularly preferred color pigments with the trade name Colorona® are, for example:
Colorona Copper, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)
Colorona RY, Merck, CI 77891 (TITANIUM DIOXIDE), MICA, CI 75470 (CARMINE)
Colorona Oriental Beige, Merck, MICA, CI 77891 (TITANIUM DIOXIDE), CI 77491 (IRON OXIDES)
Colorona Dark Blue, Merck, MICA, TITANIUM DIOXIDE, FERRIC FERROCYANIDE
Colorona Chameleon, Merck, CI 77491 (IRON OXIDES), MICA
Colorona Aborigine Amber, Merck, MICA, CI 77499 (IRON OXIDES), CI 77891 (TITANIUM DIOXIDE)
Colorona Blackstar Blue, Merck, CI 77499 (IRON OXIDES), MICA
Colorona Patagonian Purple, Merck, MICA, CI 77491 (IRON OXIDES), CI 77891 (TITANIUM DIOXIDE), CI 77510 (FERRIC FERROCYANIDE)
Colorona Red Brown, Merck, MICA, CI 77491 (IRON OXIDES), CI 77891 (TITANIUM DIOXIDE)
Colorona Russet, Merck, CI 77491 (TITANIUM DIOXIDE), MICA, CI 77891 (IRON OXIDES)
Colorona Imperial Red, Merck, MICA, TITANIUM DIOXIDE (CI 77891), D&C RED NO. 30 (CI 73360)
Colorona Majestic Green, Merck, CI 77891 (TITANIUM DIOXIDE), MICA, CI 77288 (CHROMIUM OXIDE GREENS)
Colorona Light Blue, Merck, MICA, TITANIUM DIOXIDE (CI 77891), FERRIC FERROCYANIDE (CI 77510)
Colorona Red Gold, Merck, MICA, CI 77891 (TITANIUM DIOXIDE), CI 77491 (IRON OXIDES)
Colorona Gold Plus MP 25, Merck, MICA, TITANIUM DIOXIDE (CI 77891), IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)

Colorona Bronze Fine, Merck, MICA, CI 77491 (IRON OXIDES)
Colorona Fine Gold MP 20, Merck, MICA, CI 77891 (TITANIUM DIOXIDE), CI 77491 (IRON OXIDES)
Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica, CI 77491 (Iron oxides), Tin oxide
Colorona Sun Gold Sparkle MP 29, Merck, MICA, TITANIUM DIOXIDE, IRON OXIDES, MICA, CI 77891, CI 77491 (EU)
Colorona Mica Black, Merck, CI 77499 (Iron oxides), Mica, CI 77891 (Titanium dioxide)
Colorona Bright Gold, Merck, Mica, CI 77891 (Titanium dioxide), CI 77491 (Iron oxides)
Colorona Blackstar Gold, Merck, MICA, CI 77499 (IRON OXIDES)

Particularly preferred color pigments furthermore with the trade name Unipure® are, for example:
Unipure Red LC 381 EM, Sensient CI 77491 (Iron Oxides), Silica
Unipure Black LC 989 EM, Sensient, CI 77499 (Iron Oxides), Silica
Unipure Yellow LC 182 EM, Sensient, CI 77492 (Iron Oxides), Silica Depending on which color change on the keratin fibers is desired, color pigment(s) (b) can be used in different amounts. The more pigment is employed, the greater in general the extent of the color change. Starting at a specific amount used, however, the adherence of the pigments to the keratin fibers encounters a limit, after which it is no longer possible to increase the extent of the color change by a further increase in the employed color pigment amount.

It has emerged in this regard that when zwitterionic polymers (c) are used, in particular the indicated preferred and particularly preferred representative, a film can be formed on the keratin fibers, which allows the color pigments to adhere to the keratin fibers in especially large amounts. The agents of the invention can therefore include color pigments (b) in a total amount of 1.0 to 25.0% by weight, preferably of 5.0 to 20.0% by weight, more preferably of 7.0 to 18.0% by weight, and particularly preferably of 8.5 to 15.5% by weight.

In a further particularly preferred embodiment, an agent of the invention is therefore characterized in that, based on its total weight, it includes one or more color pigments (b) in a total amount of 1.0 to 25.0% by weight, preferably of 5.0 to 20.0% by weight, more preferably of 7.0 to 18.0% by weight, and particularly preferably of 8.5 to 15.5% by weight.

The agents for temporarily changing the color of keratin fibers include at least one zwitterionic polymer as the third component (c) essential to the invention.

Polymers are understood to be macromolecules with a molecular weight of at least 1000 g/mol, preferably of at least 2500 g/mol, particularly preferably of at least 5000 g/mol, which consist of the same repeating organic units. The zwitterionic polymers of the present invention are synthetically produced polymers, which are produced by the polymerization of one monomer type or by the polymerization of various monomer types, structurally different from one another. If the polymer is prepared by the polymerization of one monomer type, the term homopolymers is used. If structurally different monomer types are used in the polymerization, the resulting polymer is called a copolymer.

The maximum molecular weight of the polymer depends on the degree of polymerization (number of polymerized monomers) and the batch size and is also determined by the polymerization method. In the context of the present invention, it is preferred if the maximum molecular weight of the cationic polymer (d) is no more than $10^7$ g/mol, preferably no more than $10^6$ g/mol, and particularly preferably no more than $10^5$ g/mol.

Zwitterionic polymers carry both cationic and anionic charges in the polymer chain or in the polymer skeleton. If the polymer includes cationic and anionic structural unit in the same molar equivalents, thus the charge equalization can occur solely by these charges located in the polymer.

If the zwitterionic polymer includes more cationic structural units than anionic structural units, thus the extra cationic charges are neutralized by the presence of corresponding equivalents of anions, such as, for example, chloride, bromide, methyl sulfate, acetate, or sulfate.

If the zwitterionic polymer includes more anionic structural units than cationic structural units, thus the extra anionic charges are neutralized by the presence of corresponding equivalents of cations, such as for, example, sodium, potassium, magnesium, calcium, ammonium, and/or trimethylammonium cations.

Zwitterionic polymers have proven to especially good for achieving the object of the invention, if they include at least one structural unit of the general formula (I'),

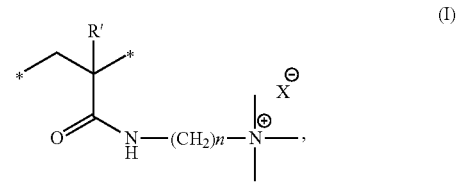

(I')

where
the R' group stands for a hydrogen atom or for a methyl group, preferably for a hydrogen atom, and
n stands for an integer from 2 to 8, preferably for the numbers 2 or 3, particularly preferably for the number 3.

The neutralization of the positive charge of the structural unit of the formula (I') can occur by a negatively charged structural unit present in the zwitterionic polymer. It is also possible, however, that the neutralization of the positive charge of the structural unit of the formula (I') can occur by the presence of a counterion X−, wherein X− can stand for a physiologically acceptable anion from the group comprising chloride, bromide, acetate, hydrogen sulfate, and ½ sulfate.

In a further very particularly preferred embodiment, an agent of the invention is characterized in that the zwitterionic polymer includes at least one structural unit of the general formula (I),

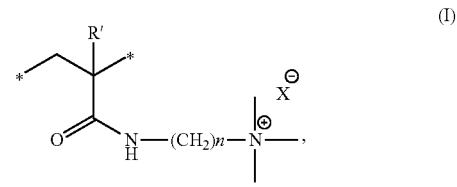

(I)

where
the R' group stands for a hydrogen atom or for a methyl group, preferably for a hydrogen atom, and
n stands for an integer from 2 to 8, preferably for the numbers 2 or 3, particularly preferably for the number 3, and
X− stands for a physiologically acceptable anion from the group comprising chloride, bromide, acetate, hydrogen sulfate, and ½ sulfate.

In a further very particularly preferred embodiment, an agent of the invention is characterized in that the zwitterionic polymer includes at least one structural unit of the general formula (I),

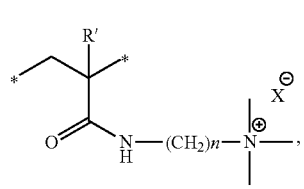
(I)

where
the R' group stands for a hydrogen atom and
n stands for the number 3.

Structural units of the general formula (I) form, for example, when during the polymerization for producing zwitterionic polymer (c) one or more monomers are used from the group comprising N,N,N-trimethyl-3-[(1-oxo-2-propenyl)amino]-1-propanaminium chloride or N,N,N-trimethyl-2-[(1-oxo-2-propenyl)amino]-1-ethanaminium chloride.

Furthermore, color pigments (b) adhere especially well to the keratinic fiber, when zwitterionic polymers (c) used to form the film include at least one structural unit of the general formula (II)

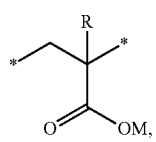
(II)

where
the R group stands for a hydrogen atom or for a methyl group, preferably for a hydrogen atom, and
the M group stands for a hydrogen atom or an equivalent of a mono- or multivalent cation of sodium, potassium, magnesium, or calcium.

Furthermore, the zwitterionic polymer (c) can also include at least one structural unit of the general formula (II')

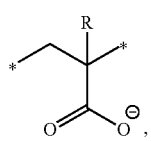
(II')

where
the R group stands for a hydrogen atom or for a methyl group, preferably for a hydrogen atom.

The neutralization of the anionic unit of the formula (II') in zwitterionic polymer (c) in this case can occur by the presence of suitable cationically charged structural units, such as, for example, a structural unit of the formula (I').

Structural units of the general formula (II) or (II') form, for example, when during the polymerization for producing zwitterionic polymer (c) one or more monomers from the group comprising acrylic acid, methacrylic acid, or salts thereof are used (such as, for example, the sodium salt of (meth)acrylic acid or the potassium salt of (meth)acrylic acid). In a further very particularly preferred embodiment, an agent of the invention is characterized in that the zwitterionic polymer includes at least one structural unit of the general formula (II),

(II)

where
the R group stands for a hydrogen atom or for a methyl group, preferably for a hydrogen atom, and
the M group stands for a hydrogen atom or an equivalent of a mono- or multivalent cation of sodium, potassium, magnesium, or calcium.

In a further very particularly preferred embodiment, an agent of the invention is characterized in that the zwitterionic polymer includes at least one structural unit of the general formula (II),

(II)

where
the R group stands for a hydrogen atom and
the M group stands for a hydrogen atom or an equivalent of a mono- or multivalent cation of sodium, potassium, magnesium, or calcium.

As previously described, particularly preferred are zwitterionic polymers that comprise at least one structural unit of the general formula (I) (or (I')) and/or at least one structural unit of the general formula (II) (or (II')). The best results were obtained with zwitterionic polymers that include both at least one structural unit of the general formula (I) (or (I')) and least one structural unit of the general formula (II) (or (II')).

The structural units of the formula (I) or of the formula (II) in this case represent the repeat units of the polymer; i.e., a polymer of the invention, therefore, usually includes the structural units of the formula (I) or of the formula (II) not only once but repeatedly.

The positions labeled with an asterisk in the formula (I) and formula (II) represent the linkage positions to the other structural units of the polymer chain. For example, two successive structural units of the formulas (I) and (II) can be linked as follows in the polymer:

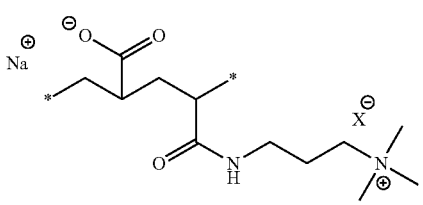

In a further very particularly preferred embodiment, an agent of the invention is characterized in that it includes a zwitterionic polymer (c) that includes at least 20 mol %, preferably at least 30 mol %, more preferably at least 40 mol %, and particularly preferably at least 50 mol % of structural units of the formula (I).

In a further very particularly preferred embodiment, an agent of the invention is characterized in that it includes a zwitterionic polymer (c) that includes at least 20 mol %, preferably at least 30 mol %, more preferably at least 40 mol %, and particularly preferably to at least 50 mol % of structural units of the formula (II).

Explicitly very particularly preferred is a polymer with the CAS number 154245-39-3. This polymer is produced by reacting the two monomers sodium acrylate (sodium salt of acrylic acid) and trimethylammoniopropylacrylamide chloride (alternative name: N,N,N-trimethyl-3-[(1-oxo-2-propenyl)amino]-1-propanaminium chloride). The polymer is sold commercially, for example, under the trade name Product W 37194 by the company Bozzetto GmbH. If this polymer was used in the agents of the invention, keratinic fibers could be dyed in metallically shiny colors, which were distinguished by especially good rubbing fastness.

Very particularly preferred is an agent for temporarily changing the color of keratinic fibers, in particular human hair, including, in an aqueous cosmetic carrier, (a) at least 35.0% by weight of ethanol, (b) at least one mica-based color pigment, which is coated with one or more metal oxides from the group comprising titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicate, CI 77007, Pigment Blue 29), chromium oxide hydrate (CI 77289), chromium oxide (CI 77288), and/or iron blue (Ferric Ferrocyanide, CI 77510), and (c) at least one zwitterionic polymer, including at least one structural unit of the general formula (I) and at least one structural unit of the general formula (II),

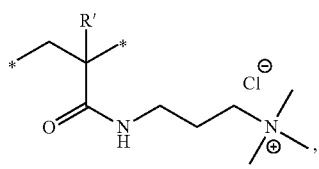

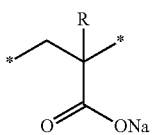

where the total amount of fatty substances (d), included in the agent, based on the total weight of the agent, has a value below 2.5% by weight.

The agents of the invention generally include zwitterionic polymer(s) (c) in a total amount of 0.1 to 10.0% by weight, preferably of 0.5 to 5.0% by weight, more preferably of 0.8 to 3.0% by weight, and particularly preferably of 1.4 to 2.6% by weight. In this regard, the quantitative data in % by weight refer to the total amount of all zwitterionic polymers (c), which are placed in relation to the total weight of the agent.

In a further particularly preferred embodiment, an agent of the invention is characterized in that, based on its total weight, it includes one or more zwitterionic polymers (c) in a total amount of 0.1 to 10.0% by weight, preferably of 0.5 to 5.0% by weight, more preferably of 0.8 to 3.0% by weight, and particularly preferably of 1.4 to 2.6% by weight.

For optimal adhesion capacity of color pigments (b) on the keratin fibers, the amounts used of color pigments (b) and zwitterionic polymers (c) are advantageously coordinated. If color pigments (b) and zwitterionic polymers (c) are used in a weight ratio of 1.0 to 6.0, thus the major part of the pigments can be bound effectively via the polymer film and immobilized in this way on the fiber. In other words, it is of particular advantage to use pigments (b) and zwitterionic polymers (c) at least in the same total amounts, or, however, to select amounts used in which the total amount of color pigments (b) exceeds the total amount of zwitterionic polymers (c) by at most a factor of 6. In the indicated weight ratio (b)/(c), the total amount of pigments (b), included in the agent, is placed in relation to the total amount of zwitterionic polymers (c) included in the agent.

In a further very particularly preferred embodiment, an agent of the invention is characterized in that the weight ratio of all color pigments (b), included in the agent, to all zwitterionic polymers (c), included in the agent, i.e., the weight ratio (b)/(c), has a value of 1.0 to 6.0, preferably of 2.0 to 5.5, more preferably of 2.5 to 5.0, and particularly preferably of 3.0 to 4.5.

Example: a temporary dyeing agent includes
35.0% by weight of water
(a) 40.0% by weight of ethanol
(b) 8.0% by weight of Colorona Bronze, Merck, MICA, CI 77491 (IRON OXIDES)
(c) 2.0% by weight of a copolymer of sodium acrylate and N,N,N-trimethyl-3-[(1-oxo-2-propenyl)amino]-1-propanaminium chloride
other ingredients to 100% by weight
Weight ratio (b)/(c)=4.0

The hair mascara products known from the prior art generally include fatty substances; these fatty substances form a film on the keratin fibers, which protects the pigments from rubbing off after application.

The essential disadvantage of the fatty substances, however, is that they produce a haptic of little advantage on the keratin fiber, which is evident particularly in a feel of hardness or an oily hair feel. The keratin fibers act as if weighed down and also visually impart the impression of oily hair.

To avoid this disadvantage, a characteristic and essential feature of the agents of the invention is that the total amount of fatty substances (d), included in the agent, based on the total weight of the agent, is a value below 2.5% by weight. "Fatty substances" in the context of the invention are understood to be organic compounds with a solubility in water at room temperature (22° C.) and atmospheric pressure (760 mm Hg) of less than 1% by weight, preferably of less than 0.1% by weight. The definition of fatty components includes explicitly only uncharged (i.e., nonionic) compounds. Charged compounds such as, for example, fatty acids and salts thereof are not understood to be a fatty component. Fatty substances have at least one saturated or unsaturated alkyl group having at least 12 C atoms.

If the fatty substances include an unsaturated alkyl group, thus this may have one or more double bonds. The molar weight of the fatty components is a maximum of 5000 g/mol, preferably a maximum of 2500 g/mol, and particularly preferably a maximum of 1000 g/mol. The fatty components are neither polyoxyalkylated nor polyglycerylated compounds; i.e., fatty alcohols or fatty acids that are esterified or etherified with at least two oxyalkyl groups or with at least two glycerol units do not fall under the definition of fatty substances.

Fatty substances (d) include $C_{12}$-$C_{30}$ fatty alcohols. $C_{12}$-$C_{30}$ fatty alcohols are saturated, mono- or polyunsaturated, linear or branched fatty alcohols having 12 to 30 C atoms. Examples of $C_{12}$-$C_{30}$ fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachidyl alcohol (eicosan-1-ol), heneicosyl alcohol (heneicosan-1-ol), and/or behenyl alcohol (docosan-1-ol). Examples of branched fatty alcohols are 2-octyldodecanol, 2-hexyldodecanol, and/or 2-butyldodecanol. Fatty substances (d) also include $C_{12}$-$C_{30}$ fatty acid triglycerides. A $C_{12}$-$C_{30}$ fatty acid triglyceride is understood to be the triester of the trihydric alcohol, glycerol, with three fatty acid equivalents. In this regard, both structurally similar and also different fatty acids can be involved in ester formations within a triglyceride molecule. Fatty substances also include $C_{12}$-$C_{30}$ fatty acid diglycerides. A $C_{12}$-$C_{30}$ fatty acid diglyceride is understood to be the diester of the trihydric alcohol, glycerol, with two fatty acid equivalents. In this regard, both structurally similar and also different fatty acids can be involved in ester formations within a diglyceride molecule. Fatty substances also include $C_{12}$-$C_{30}$ fatty acid monoglycerides. A $C_{12}$-$C_{30}$ fatty acid monoglyceride is understood to be the monoester of the trihydric alcohol, glycerol, with one fatty acid equivalent.

Fatty substances (d) also include the diesters of an equivalent of ethylene glycol (1,2-ethanediol) with two equivalents of fatty acid (ethylene glycol difatty acid ester). In this case, both structurally identical and different fatty acids can be involved in the ester bonds to ethylene glycol.

Fatty substances (d) also include waxes. Waxes are understood to be the esters of $C_{12}$-$C_{30}$ fatty acids with $C_{12}$-$C_{30}$ fatty alcohols.

Fatty substances (d) also include hydrocarbons having at least 12 C atoms. Hydrocarbons are compounds consisting exclusively of the atoms carbon and hydrogen. Examples of hydrocarbons are mineral oils, liquid paraffin oils (e.g., liquid paraffin or light liquid paraffin), isoparaffin oils, semisolid paraffin oils, paraffin waxes, hard paraffin (solid paraffin), Vaseline, and polydecene.

Silicones are not covered by the definition of fatty substances.

Accordingly, an agent according to the invention is one for temporarily changing the color of keratinic fibers, in particular human hair, including, in an aqueous cosmetic carrier,
(a) at least one aliphatic and/or aromatic alcohol having 2 to 8 C atoms,
(b) at least one color pigment, and
(c) at least one zwitterionic polymer,
wherein
the total amount of fatty substances (d), included in the agent, from the group comprising $C_{12}$-$C_{30}$ fatty alcohols, $C_{12}$-$C_{30}$ fatty acid triglycerides, $C_{12}$-$C_{30}$ fatty acid diglycerides, $C_{12}$-$C_{30}$ fatty acid monoglycerides, ethylene glycol difatty acid esters, waxes, and hydrocarbons has a value below 2.5% by weight.

Small amounts of fatty substances can be introduced potentially into the agents of the invention by the use of certain raw materials. So as to weigh down the hair as little as possible, it is preferred, however, to keep the use of fatty substances (d) where possible as low as possible. It is preferred, therefore, if the total amount of fatty substances (d) in the agent has a value below 2.0% by weight, preferably below 1.5% by weight, more preferably below 0.5% by weight, and particularly preferably below 0.1% by weight. The weight data in this case refer to the total amount of all fatty substances (d), placed in relation to the total weight of the agent.

In a further very particularly preferred embodiment, an agent of the invention is therefore characterized in that the total amount of all fatty substances (d), included in the agent, in particular fatty substances from the group comprising $C_{12}$-$C_{30}$ fatty alcohols, $C_{12}$-$C_{30}$ fatty acid triglycerides, $C_{12}$-$C_{30}$ fatty acid diglycerides, $C_{12}$-$C_{30}$ fatty acid mono glycerides, ethylene glycol difatty acid esters, waxes, and hydrocarbons has a value below 2.0% by weight, preferably below 1.5% by weight, more preferably below 0.5% by weight, and particularly preferably below 0.1% by weight.

Particularly preferred as well is an agent for temporarily changing the color of keratinic fibers, in particular human hair, including, in an aqueous cosmetic carrier,
(a) at least 35.0% by weight of ethanol,
(b) at least one color pigment, and
(c) at least one zwitterionic polymer,
where
the total amount of fatty substances (d), included in the agent, from the group comprising $C_{12}$-$C_{30}$ fatty alcohols, $C_{12}$-$C_{30}$ fatty acid triglycerides, $C_{12}$-$C_{30}$ fatty acid diglycerides, $C_{12}$-$C_{30}$ fatty acid monoglycerides, ethylene glycol difatty acid esters, waxes, and hydrocarbons has a value below 0.5% by weight.

Also very particularly preferred is an agent for temporarily changing the color of keratinic fibers, in particular human hair, including, in an aqueous cosmetic carrier,
(a) at least 45.0% by weight of ethanol,
(b) at least one color pigment, and
(c) at least one zwitterionic polymer,
where
the total amount of fatty substances (d), included in the agent, from the group comprising $C_{12}$-$C_{30}$ fatty alcohols, $C_{12}$-$C_{30}$ fatty acid triglycerides, $C_{12}$-$C_{30}$ fatty acid diglycerides, $C_{12}$-$C_{30}$ fatty acid monoglycerides, ethylene glycol difatty acid esters, waxes, and hydrocarbons has a value below 0.5% by weight.

The agents are provided as aqueous-alcoholic preparations. Optionally, one further surface-active substance can be added in addition to the agents, wherein such surface-active substances are called surfactants or emulsifiers depending on the field of application. Preferably, the agents of the invention include in addition at least one nonionic surfactant and/or a cationic surfactant. The use of anionic surfactants proved to be less advantageous.

The agents of the invention can include in addition at least one nonionic surfactant. Suitable nonionic surfactants are alkyl polyglycosides and alkylene oxide adducts to fatty alcohols and fatty acids with in each case 2 to 30 mol of ethylene oxide per mole of fatty alcohol or fatty acid. Preparations with good properties are also obtained, if they include as nonionic surfactants fatty acid esters of ethoxylated glycerol, which was a reacted with at least 2 mol of ethylene oxide.

The nonionic surfactants are used in amounts of 0.1 to 45% by weight, preferably 1 to 30% by weight and very particularly preferably of 1 to 15% by weight, based on the total weight of the agent.

The agents of the invention can include in addition at least one cationic surfactant. Cationic surfactants are understood to be surfactants, therefore surface-active compounds, in each case with one or more positive charges. Cationic surfactants include solely positive charges. These surfactants are usually made up of a hydrophobic part and a hydrophilic head group, wherein the hydrophobic part generally consists of a hydrocarbon skeleton (e.g., consisting of one or two linear or branched alkyl chains), and the positive charge(s) is (are) localized in the hydrophilic head group.

Examples of cationic surfactants are
  quaternary ammonium compounds, which can carry as hydrophobic groups one or two alkyl chain with a chain length of 8 to 28 C atoms,
  quaternary phosphonium salts, substituted with one or more alkyl chains with a chain length of 8 to 28 C atoms, or
  tertiary sulfonium salts.

Furthermore, the cationic charge in the form of an onium structure as well can be part of a heterocyclic ring (e.g., an imidazolium ring or a pyridinium ring).

Apart from the functional unit carrying the cationic charge, the cationic surfactants can also include other uncharged functional groups, as is the case, for example, with esterquats.

The cationic surfactants are used in amounts of 0.1 to 45% by weight, preferably 1 to 30% by weight, and very particularly preferably of 1 to 15% by weight, based on the total weight of the agent.

The use of anionic surfactants has proven to be disadvantageous in regard to the abrasion resistance of pigments on keratinic fibers. It is preferred for this reason not to use any anionic surfactants in the agents of the invention.

Surface-active agents with exclusively anionic charges (neutralized by a corresponding countercation) are designated as anionic surfactants.

Examples of anionic surfactants are fatty acids, alkyl sulfates, alkyl ether sulfates, and ether carboxylic acids having 12 to 20 C atoms in the alkyl group and up to 16 glycol ether groups in the molecule.

In a further preferred embodiment, agents of the invention are characterized in that the total amount of all anionic surfactants, included in the agent, has a value below 2.5% by weight, preferably below 1.5% by weight, more preferably below 0.5% by weight, and particularly preferably below 0.1% by weight, all quantitative data being referred to the total weight of the agent.

The agents of the invention can include, furthermore, at least one zwitterionic and/or amphoteric surfactant.

Suitable zwitterionic surfactants are betaines, N-alkyl-N, N-dimethylammonium glycinates, N-acylaminopropyl-N, N-dimethylammonium glycinates, and 2-alkyl-3-carboxymethyl-3-hydroxyethyl imidazolines. A preferred zwitterionic surfactant is known by the INCI name Cocamidopropyl Betaine.

Suitable amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids, and alkylaminoacetic acids. Particularly preferred amphoteric surfactants are N-cocoalkyl aminopropionate, cocoacylaminoethyl aminopropionate, and $C_{12}$-$C_{18}$ acylsarcosine.

The amphoteric and/or zwitterionic surfactants are used in amounts of 0.1 to 45% by weight, preferably 1 to 30% by weight, and very particularly preferably of 1 to 15% by weight, based on the total weight of the agent.

An advantage of the agents of the invention is that they can be produced in many forms. Very uniform color effects and abrasion-resistant colors can be achieved by application using a sponge or a small brush. Likewise, it is also possible, however, to produce the agents of the invention as a spray. In particular, colors obtained by spray application are also distinguished by a very high uniformity.

Depending on the selected application form, the agents of the invention are adjusted to a specific viscosity. This generally occurs through the use of one or more thickeners. There are no basic restrictions in regard to these thickeners. Both organic and purely inorganic thickeners may be used.

Suitable thickeners are anionic, synthetic polymers; cationic, synthetic polymers; naturally occurring thickeners, such as nonionic guar gums, scleroglucan gums or xanthan gums, gum arabic, gum ghatti, karaya gum, tragacanth gum, carrageenan gum, agar-agar, locust bean flour, pectins, alginates, starch fractions, and derivatives such as amylose, amylopectin, and dextrins, as well as cellulose derivatives (which are different from the celluloses of the invention) such as, for example, methylcellulose, carboxyalkylcelluloses, and hydroxyalkylcelluloses; nonionic, fully synthetic polymers such as polyvinyl alcohol or polyvinylpyrrolidinone; as well as inorganic thickeners, in particular phyllosilicates such as, for example, bentonite, in particular smectites, such as montmorillonite or hectorite.

The viscosity of the agents can be adjusted especially easily and reproducibly by polysaccharides, especially polysaccharides from the group comprising carboxy-C1-C6-alkyl celluloses, hydroxy-$C_2$-$C_8$-alkyl celluloses, alginic acids, and/or xanthan gum.

By variation of the employed polysaccharide amount, the agent can be produced both as a gel for brush or sponge application or also, however, as a low-viscosity, sprayable solution. The other formulation components or their amounts used need not be adjusted in this case. This is of advantage in particular in the production of the agents.

In a further particularly preferred embodiment, an agent of the invention is therefore characterized in that it includes as a thickener in addition at least one polysaccharide from the group comprising carboxy-$C_1$-$C_6$-alkyl celluloses, hydroxy-$C_2$-$C_8$-alkyl celluloses, alginic acids, and/or xanthan gum.

In a very particularly preferred embodiment, an agent of the invention is therefore characterized in that it includes as a thickener in addition at least one polysaccharide from the group of hydroxy-$C_2$-$C_8$-alkyl celluloses.

The thickener(s) can be used in the agents of the invention in a total amount of 0.1 to 4.5% by weight, preferably of 0.15 to 3.5% by weight, and particularly preferably of 0.2 to 2.0% by weight, based on the total weight of the agent.

The agents of the invention can include one or more alkalizing agents for adjusting the pH value. The alkalinizing agents that can be used to adjust the desired pH value can be selected from the group formed by ammonia, alkanolamines, basic amino acids, and inorganic alkalinizing agents such as alkali (alkaline earth) metal hydroxides, alkali (alkaline earth) metal metasilicates, alkali (alkaline earth)

metal phosphates, and alkali (alkaline earth) metal hydrogen phosphates. The agents of the invention can include one or more acids to adjust the pH value. Suitable acids are, for example, organic acids such as alpha-hydroxycarboxylic acids or inorganic acids.

Furthermore, the agents can include one or more nonionic polymers.

Suitable nonionogenic polymers are, for example:
vinylpyrrolidone/vinyl ester copolymers, as they are marketed, for example, under the trademark Luviskol® (BASF). Luviskol® VA 64 and Luviskol® VA 73, each being vinylpyrrolidone/vinyl acetate copolymers, are also preferred nonionic polymers;
starch and derivatives thereof, in particular starch ethers, for example, Structure® XL (National Starch), a multifunctional, salt-tolerant starch;
shellac;
polyvinylpyrrolidones, as they are marketed, for example, under the name Luviskol® (BASF).

Furthermore, agents (V) and/or (F) can include one or more polymers from the group comprising Polyquaternium-1, Polyquaternium-2, Polyquaternium-3, Polyquaternium-4, Polyquaternium-5, Polyquaternium-6, Polyquaternium-7, Polyquaternium-8, Polyquaternium-9, Polyquaternium-10, Polyquaternium-11, Polyquaternium-14, Polyquaternium-16, Polyquaternium-17, Polyquaternium-18, Polyquaternium-22, Polyquaternium-24, Polyquaternium-27, Polyquaternium-28, Polyquaternium-32, Polyquaternium-33, Polyquaternium-37, Polyquaternium-39, Polyquaternium-44, Polyquaternium-46, Polyquaternium-53, Polyquaternium-55, Polyquarternium-64, Polyquaternium-67, Polyquaternium-68, Polyquaternium-69, and/or Polyquaternium-86.

Further, the agents of the invention may include other active substances, auxiliary substances, and additives such as, for example, linear cationic polymers such as quaternized cellulose ethers, polysiloxanes with quaternary groups, dimethyldiallylammonium chloride polymers, acrylamide-dimethyldiallylammonium chloride copolymers, dimethylaminoethyl methacrylate-vinylpyrrolidinone copolymers quaternized with diethyl sulfate, vinylpyrrolidone-imidazolinium-methochloride copolymers, and quaternized polyvinyl alcohol; zwitterionic and amphoteric polymers (which are different from the zwitterionic polymers of the invention); anionic polymers such as, for example, polyacrylic acids or crosslinked polyacrylic acids; structurants such as glucose, maleic acid, and lactic acid, hair-conditioning compounds such as phospholipids, for example, lecithin and kephalins; perfume oils, dimethyl isosorbide, and cyclodextrins; fiber-structure-improving active substances, particularly mono-, di-, and oligosaccharides such as, for example, glucose, galactose, fructose, fruit sugar, and lactose; dyes for coloring the agent; antidandruff agents such as piroctone olamine, zinc omadine, and climbazole; amino acids and oligopeptides; protein hydrolysates with an animal and/or vegetable base, and in the form of their fatty acid condensation products or optionally anionically or cationically modified derivatives; light stabilizers and UV blockers; active substances such as panthenol, pantothenic acid, pantolactone, allantoin, pyrrolidinone carboxylic acids and salts thereof, as well as bisabolol; polyphenols, particularly hydroxycinnamic acids, 6,7-dihydroxycoumarins, hydroxybenzoic acids, catechins, tannins, leukoanthocyanidins, anthocyanidins, flavanones, flavones, and flavonols; ceramides or pseudoceramides; vitamins, provitamins, and vitamin precursors; plant extracts; fats and waxes such as fatty alcohols, beeswax, montan wax, and paraffins; swelling and penetration agents such as glycerol, propylene glycol monoethyl ethers, carbonates, hydrogen carbonates, guanidines, ureas, and primary, secondary, and tertiary phosphates; opacifiers such as latex, styrene/PVP and styrene/acrylamide copolymers, and PEG-3 distearate; propellants such as propane-butane mixtures, $N_2O$, dimethyl ether, $CO_2$, and air.

The selection of these additional substances is made by the skilled artisan according to the desired properties of the agents. In regard to other facultative components and the employed amounts of said components, reference is made expressly to relevant handbooks known to the skilled artisan. The additional active and auxiliary substances are used in the agents of the invention preferably in each case in amounts of 0.0001 to 25% by weight, in particular of 0.0005 to 15% by weight, based on the total weight of the particular agent.

The products of the invention can be produced, for example, in the form of a gel, a spray, an aerosol, or a pump foam. Depending on the application form, they are therefore preferably filled into a tube, a container, a bottle, a box, a pressurized container, or into a container with a pump spray applicator.

If the products are applied in spray form, the pigments can be applied especially uniformly to the keratinic fibers. The production as an aerosol or as a pump spray therefore is very particularly preferred.

In the aforementioned preferred embodiment, the product of the invention comprises a pressurized container. Vessels made of metal (aluminum, tin plate, tin), of protected or non-splintering plastic, or of glass that is externally coated with plastic may be used as compressed-gas containers; pressure resistance and breaking strength, corrosion resistance, ease of filling, as well as aesthetic aspects, handling, printability, etc., play a role in their selection. Special protective interior coatings can assure corrosion resistance against the preparation within the pressurized container.

If the product of the invention is applied via a pressurized container, the agents include in addition at least one propellant gas from the group comprising propane, propene, n-butane, isobutane, isobutene, n-pentane, pentene, isopentane, isopentene, air, nitrogen, argon, $N_2O$, and/or $CO_2$. Within this group, the permanent gases: air, nitrogen, argon, $N_2O$, and/or $CO_2$ are preferred; nitrogen, argon, and/or $CO_2$ are very particularly preferred.

Furthermore, the agents of the invention can also be provided for use in the form of a pump spray. Suitable containers with pumps or a squeeze mechanism are commercially available, for example, from the company Rexam SMT or Seaquist.

During use in the form of a pump spray or in the form of an aerosol spray, the user can spray the agents of the invention directly onto dry hair and in this way produce the desired temporary color change.

In this regard, the user can first shape his/her hairstyle, for example, by combing, teasing, or by using a curling iron, and then spray on the agent of the invention. It is likewise possible to first spray on the agent of the invention and after or during the spraying to shape the hairstyle by the aforementioned methods.

A second subject of the present invention, therefore, is a method for temporarily changing the color and shape of hair, wherein an agent of the first subject of the invention, which is produced in the form of a pump spray or aerosol spray, is sprayed onto dry hair and the hair is styled before or during the application. The statements made regarding the agents of the invention apply mutatis mutandis with respect to the further preferred embodiments of the method of the invention.

EXAMPLES

The following formulations were prepared; all data are provided, unless specified otherwise, as a percent by weight (active substance).

1. Sponge Application

| | % by weight |
|---|---|
| Stearamidopropyl dimethylamine | 1.3 |
| Lactic acid | 0.3 |
| Copolymer of sodium acrylate and N,N,N-trimethyl-3-[(1-oxo-2-propenyl)amino]-1-propanaminium chloride (Product W 37194, Bozzetto GmbH) | 20 |
| Glycerol | 2.0 |
| Cetyltrimethylammonium chloride | 0.45 |
| PEG-7 Glyceryl Cocoate | 2.0 |
| Hydroxyethylcellulose | 0.2 |
| Colorona Precious Gold (Merck, Mica, CI 77891 (Titanium dioxide), Silica, CI 77491 (Iron oxides), Tin oxide) | 8.5 |
| Ethanol | 51 |
| Water | To 100 |

The formulation was applied using a sponge to dry hair strands (Kerling dark blonde). A uniformly colored strand with a golden sheen was obtained.

2. Brush Application

| | % by weight |
|---|---|
| Stearamidopropyl dimethylamine | 1.3 |
| Lactic acid | 0.3 |
| Copolymer of sodium acrylate and N,N,N-trimethyl-3-[(1-oxo-2-propenyl)amino]-1-propanaminium chloride (Product W 37194, Bozzetto GmbH) | 2.0 |
| Glycerol | 2.0 |
| Cetyltrimethylammonium chloride | 0.45 |
| PEG-7 Glyceryl Cocoate | 2.0 |
| Hydroxyethylcellulose | 2.0 |
| Colorona Precious Gold (Merck, Mica, CI 77891 (Titanium dioxide), Silica, CI 77491 (Iron oxides), Tin oxide) | 8.5 |
| Ethanol | 51 |
| Water | To 100 |

The formulation was applied using a small brush to a dry hair strand (Kerling dark blonde). A uniformly colored strand with a golden sheen was obtained.

3. Spray Application

| | % by weight |
|---|---|
| Stearamidopropyl dimethylamine | 1.3 |
| Lactic acid | 0.3 |
| Copolymer of sodium acrylate and N,N,N-trimethyl-3-[(1-oxo-2-propenyl)amino]-1-propanaminium chloride (Product W 37194, Bozzetto GmbH) | 2.0 |
| Glycerol | 2.0 |
| Cetyltrimethylammonium chloride | 0.45 |
| PEG-7 Glyceryl Cocoate | 2.0 |
| Colorona Precious Gold (Merck, Mica, CI 77891 (Titanium dioxide), Silica, CI 77491 (Iron oxides), Tin oxide) | 8.5 |
| Ethanol | 51 |
| Water | To 100 |

The formulation was filled into a pump sprayer and sprayed onto a dry hair strand (Kerling dark blonde). A uniformly colored strand with a golden sheen was obtained.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for temporarily changing the color and shape of hair, including
    spraying an agent, which is produced in the form of a pump spray or aerosol spray, onto dry hair, and
    styling the hair before or during the application
   wherein the agent, in an aqueous cosmetic carrier, comprises,
    (a) at least one aliphatic and/or aromatic alcohol having 2 to 8 C atoms,
    (b) at least one color pigment, and
    (c) at least one zwitterionic polymer,
    wherein the total amount of fatty substances (d), included in the agent, based on the total weight of the agent, has a value below 2.5% by weight.

2. The method according to claim 1, wherein the one or more alcohols (a) are selected from the group consisting of ethanol, isopropanol, n-propanol, butanol, n-pentanol, 1-propanediol, 1,3-propanediol, 1,3-butanediol, 1,4-butanediol, 1,2-hexanediol, 1,6-hexanediol, glycerol, benzyl alcohol, phenoxyethanol, and phenethyl alcohol.

3. The method according to claim 1, wherein the agent includes the one or more alcohols (a) in a total amount of at least 10.0% by weight.

4. The method according to claim 2, wherein the agent includes the one or more alcohols (a) in a total amount of at least 50.0% by weight.

5. The method according to claim 1, wherein the agent includes at least 15.0% by weight ethanol.

6. The method according to claim 1, wherein the agent includes 1,2-propanediol and/or glycerol in a total amount of 0.1 to 7.0% by weight.

7. The method according to claim 1, wherein the agent has a water content between 20 and 60% by weight.

8. The method according to claim 1, wherein the agent includes as the color pigment (b) at least one inorganic color pigment, which is selected from the group consisting of colored metal oxides, metal hydroxides, metal oxide hydrates, silicates, metal sulfides, complex metal cyanides, metal sulfates, bronze pigments, and colored mica-based pigments, which are coated with at least one metal oxide and/or a metal oxychloride.

9. The method according to claim 1, wherein the agent includes as the color pigment (b) at least one mica-based color pigment, which is coated with one or more metal oxides selected from the group consisting of titanium dioxide (CI 77891), black iron oxide (CI 77499), yellow iron oxide (CI 77492), red iron oxide (CI 77491), brown iron oxide (CI 77499), manganese violet (CI 77742), ultramarine (sodium aluminum sulfosilicate, CI 77007, Pigment Blue 29), chromium oxide hydrate (CI 77289), chromium oxide (CI 77288), and iron blue (Ferric Ferrocyanide, CI 77510).

10. The method according to claim 1, wherein the agent includes the at least one color pigment (b) in a total amount of 1.0 to 25.0% by weight.

11. The method according to claim 1, wherein the zwitterionic polymer (c) includes at least one structural unit of the general formula (I),

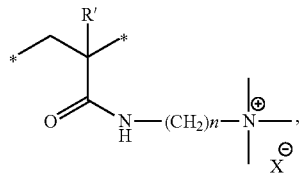

(I)

wherein the R' group stands for a hydrogen atom or for a methyl group, n stands for an integer from 2 to 8, and X— stands for a physiologically acceptable anion selected from the group consisting of chloride, bromide, acetate, hydrogen sulfate, and ½ sulfate.

12. The method according to claim 1, wherein the zwitterionic polymer (c) includes at least one structural unit of the general formula (II),

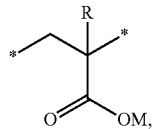

(II)

wherein

R is a hydrogen atom or a methyl group, and

M is a hydrogen atom or an equivalent of a mono- or multivalent cation of sodium, potassium, magnesium, or calcium.

13. The method according to claim 11, wherein the zwitterionic polymer (c) includes at least 20 mol % of structural units of the formula (I).

14. The method according to claim 12, wherein the zwitterionic polymer (c) includes at least 20 mol % of structural units of the formula (II).

15. The method according to claim 1, wherein all of the fatty substances (d), included in the agent are fatty substances selected from the group consisting of $C_{12}$-$C_{30}$ fatty alcohols, $C_{12}$-$C_{30}$ fatty acid triglycerides, $C_{12}$-$C_{30}$ fatty acid diglycerides, $C_{12}$-$C_{30}$ fatty acid monoglycerides, ethylene glycol difatty acid esters, waxes, and hydrocarbons, and wherein the fatty substances (d) are included at a concentration of below 2.0% by weight with respect to the total weight of the agent.

* * * * *